United States Patent [19]

Fujii et al.

[11] Patent Number: 4,634,783

[45] Date of Patent: * Jan. 6, 1987

[54] NOVEL AMIDINE COMPOUND

[75] Inventors: Setsuro Fujii, Toyonaka; Toyoo Nakayama, Funabashi; Shigeki Nunomura, Chiba; Ryoji Matsui, Ichikawa; Shin-ichi Watanabe; Kimio Sudo, both of Funabashi; Toshiyuki Okutome, Tokyo; Masateru Kurumi, Narita; Yojiro Sakurai, Kamakura; Takuo Aoyama, Sakura, all of Japan

[73] Assignee: Torii & Co. Ltd., Tokyo, Japan

[*] Notice: The portion of the term of this patent subsequent to Jan. 7, 2003 has been disclaimed.

[21] Appl. No.: 573,268

[22] Filed: Jan. 23, 1984

[30] Foreign Application Priority Data

Jan. 28, 1983 [JP] Japan .................................. 58-12190

[51] Int. Cl.$^4$ ................. C07D 307/54; C07D 307/56; C07D 307/64; C07D 307/66

[52] U.S. Cl. .................................. 549/475; 546/290; 546/314; 549/32; 546/329; 546/168; 549/77; 546/174; 546/192; 549/304; 546/205; 544/253; 549/476; 544/35; 549/478; 549/479; 549/481; 549/483; 549/484; 549/491; 549/494; 549/467; 549/468; 549/291; 549/293; 549/57; 548/532; 548/560; 548/469; 548/490; 548/531; 548/335; 548/341; 548/333; 548/152; 548/236; 548/225; 548/217; 544/336; 544/406; 544/37; 544/56

[58] Field of Search ...................... 549/479, 484, 494; 514/469, 470, 471, 473, 825, 475, 481, 476, 483, 484, 479, 491, 494

[56] References Cited

U.S. PATENT DOCUMENTS 4,131,673 12/1978 Okamoto et al. ................. 514/224
4,214,093 6/1980 Fujii et al. ........................ 560/34
4,256,887 3/1981 Novello et al. ................... 514/825
4,433,152 2/1984 Muramatsu et al. .............. 546/227
4,454,338 6/1984 Fujii et al. ........................ 560/34
4,490,388 12/1984 Fujii et al. ........................ 549/436
4,496,584 1/1985 Fujii et al. ........................ 514/510
4,514,416 4/1985 Fujii et al. ........................ 549/442
4,532,255 7/1985 Fujii et al. ........................ 514/466
4,563,527 1/1986 Fujii et al. ........................ 546/169
4,570,006 2/1986 Fujii et al. ........................ 549/442

FOREIGN PATENT DOCUMENTS 048433 3/1982 European Pat. Off. .
067561 12/1982 European Pat. Off. .
071433 2/1983 European Pat. Off. .
2098983 12/1982 United Kingdom .

Primary Examiner—Glennon H. Hollrah
Assistant Examiner—D. Dinner
Attorney, Agent, or Firm—Beveridge, DeGrandi & Weilacher

[57] ABSTRACT

Amidine compounds of the formula

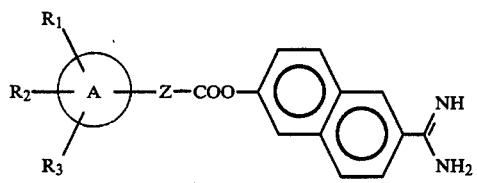

and pharmaceutically acceptable acid addition salts thereof are novel compounds and are useful as powerful anti-trypsin, anti-plasmin, anti-kallikrein and anti-thrombin agents. They are also useful as a powerful anti-complement agent.

1 Claim, No Drawings

NOVEL AMIDINE COMPOUND

This invention relates to novel amidine compounds of formula (I)

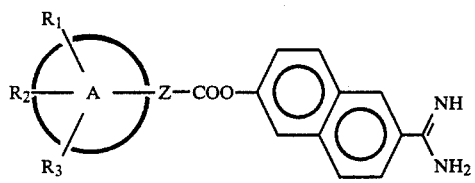

and pharmaceutically acceptable acid addition salts thereof.

In above formula (I), $R_1$, $R_2$ and $R_3$ each represent a hydrogen atom, $R_4$, halogen, $NO_2$,

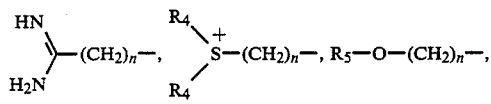

$R_4$ represents an alkyl group; $R_5$ represents a hydrogen atom, an alkyl group or a benzyl group; $R_6$ represents an alkyl group,

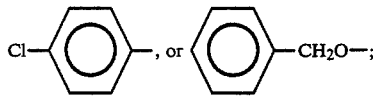

$R_7$ represents an alkyl group or

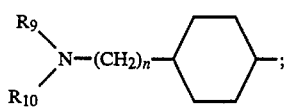

$R_8$ represents a hydrogen atom, $NO_2$ or a guanidino group; X represents a single bond, $-(CH_2)_2-$ or $-CH=CH-$; n is 0 to 4; $R_9$ and $R_{10}$ each represent a hydrogen atom or an amino radical protecting group; Z represents a single bond, an alkylene, alkenylene or alkynylene group,

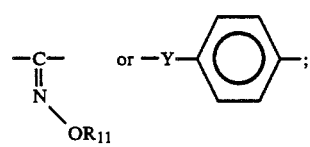

$R_{11}$ represents an alkyl group; Y represents an alkylene group; and A represents a heterocyclic ring.

The heterocyclic ring in formula (I) is preferably a single heterocyclic ring or a heterocyclic ring condensed by one or two benzene rings and/or other heterocyclic rings, more preferably a heterocyclic ring containing one or two hetero atoms, which may be the same or different, O, S or N.

Examples of the single heterocyclic ring include

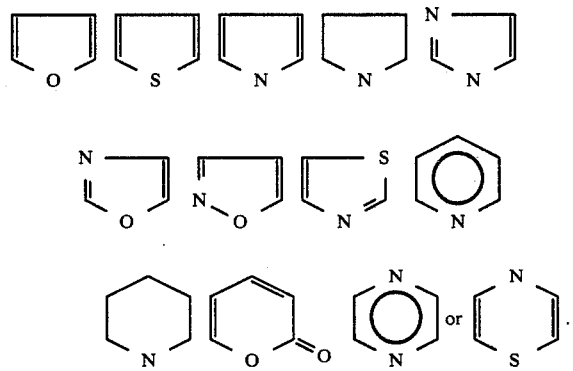

Examples of the heterocyclic ring condensed by one or two benzene rings and/or other heterocyclic rings include

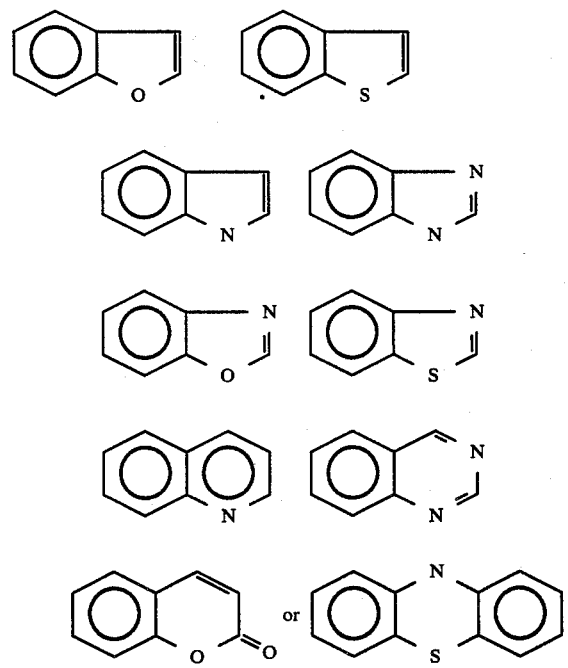

The alkylene, alkenylene, alkynylene or alkyl group for Z in formula (I) is preferably a straight or branched chain alkylene, alkenylene, alkynylene or alkyl group of 1 to 4 carbon atoms. Examples of Z include a single bond, $-CH_2-$, $-(CH_2)_2-$, $-(CH_2)_3-$, $-CH=CH-$,

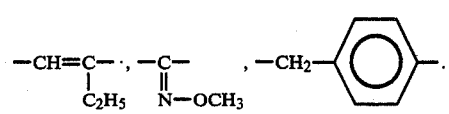

$R_1$, $R_2$ and $R_3$, which may be the same or different, represent each a hydrogen atom, $R_4$, halogen, $NO_2$, $R_4$, $R_5$, $R_6$, $R_7$, $R_8$ and n are as defined above.

An alkyl group contained in $R_1$, $R_2$ or $R_3$ is preferably a straight or branched chain alkyl group of 1 to 4 carbon atoms.

An amino radical protecting group for $R_9$ or $R_{10}$ is preferably $R_{12}CO-$, wherein $R_{12}$ is an alkyl group, a benzyloxycarbonyl or t-butoxycarbonyl group.

Examples of the following groups include $CH_3$ for $R_4$; Cl or Br for halogen;

[Structural formulas showing various group examples]

An object of this invention is to provide pharmaceutically useful novel amidino compounds and pharmaceutically acceptable acid addition salts thereof.

Another object of this invention is to provide a process for producing said novel amidino compounds.

Still another object of this invention is to provide powerful anti-trypsin, anti-plasmin, anti-kallikrein and anti-thrombin agents.

A further object of this invention is to provide powerful anti-complement agents.

The compound (I) of this invention can be produced by the reaction between a carboxylic acid compound of the formula (II) or a reactive intermediate thereof and 6-amidino-2-naphthol of the formula (III) or preferably an acid addition salt thereof.

[Structural formulas of compounds (II) and (III) with reaction arrow to (I)]

$R_1$, $R_2$, $R_3$, A and Z are as defined above. The reactive intermediates, as herein referred to, include acid halides and acid anhydrides commonly used in the dehydration. condensation and the reactive intermediates formed by reacting dicyclohexyl carbodiimide (DCC), diphenyl phosphorylazide (DPPA), or the like with a carboxylic acid derivative.

The process for producing the present compound is described below in detail.

The present compound (I) can be prepared by dissolving or suspending a carboxylic acid compound (II) in an organic solvent such as dimethylformamide, pyridine, or the like, then allowing the compound (II) to react with an carboxylic acid activator such as dicyclohexylcarbodiimide (DCC), diphenylphosphoryl azide (DPPA), or the like, which is usually used as dehydration-condensation agent, and adding 6-amidino-2-naphthol (III) or preferably an acid addition salt thereof to the reaction product.

For instance, when DCC is used as the dehydration-condensation agent, a carboxylic acid derivative (II) is added to a solvent such as pyridine, then 6-amidino-2-naphthol (III) is added, and the mixture is stirred at a temperature between −30° and 80° C., preferably at room temperature, for 3 to 5 hours to complete the reaction, though it is not objectionable to continue the reaction overnight. Dicyclohexylurea (DCU) precipitates out of the reaction mixture, while the present compound (I) either precipitates with DCU or remains dissolved in the solvent. In the former case, both precipitates are collected by filtration, then suspended in a suitable solvent such as dimethylformamide or the like and the mixture is filtered to remove insoluble DCU. After adding to the filtrate a solvent such as ethyl ether, ethyl acetate, acetone or the like, the precipitate is collected by filtration to obtain the present compound (I). Alternatively, the combined precipitate of DCU and the present compound (I) is collected by filtration, then added to a suitable solvent such as dimethylformamide, water or the like to remove insoluble DCU by filtration, the filtrate is added to a saturated aqueous sodium hydrogencarbonate solution to obtain the present compound (I) in the form of carbonate. In the latter case, where the present compound remains dissolved in the reaction mixture, DCU is removed by filtration and the filtrate is admixed with a solvent such as ethyl ether, acetone, ethyl acetate, or the like to obtain the present compound (I).

In another process, when it is intended to use an acid halide as a reactive intermediate of a carboxylic acid derivative (II), the latter derivative (II) is allowed to react with an acidhalogenation agent such as $SOCl_2$, $SOBr_2$, $PCl_5$ or the like to synthesize an acid halide represented by the formula (IV)

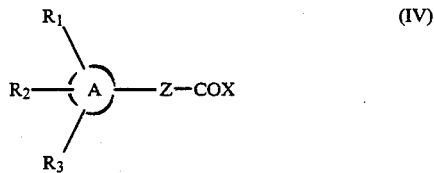

wherein $R_1$ and Z are as defined above and X represents a halogen atom. The acid halide is added to a solution of 6-amidino-2-naphthol (III), preferably in the form of an acid addition salt, dissolved in dimethylformamide, pyridine, dimethyl sulfoxide or the like and allowed to react in the presence of a dehydrohalogenation agent. The dehydrohalogenation agents which can be used include inorganic bases such as potassium carbonate, sodium carbonate, sodium hydroxide and the like and organic bases such as triethylamine, pyridine, dimethylaniline and the like. Of these bases, pyridine is preferred. Although the reaction proceeds readily at a temperature in the range of −30° to 80° C., it is preferable for the purpose of avoiding side reactions to conduct the reaction in the early stage under ice cooling and then at room temperature. The reaction is complete in 2 to 5 hours, though the reaction mixture can be left overnight. After completion of the reaction, the reaction mixture is treated in a customary manner. For instance, when pyridine was used as the reaction medium, a solvent such as ethyl ether or ethyl acetate is added to the reaction mixture to precipitate a solid reaction product which is then recrystallized from a suitable solvent such as a methanol-ethyl ether mixture to obtain the present compound (I).

The compound (III) is replaced by the corresponding compound wherein an amidino group is protected, and the latter compound can be allowed to react with the compound (II) to obtain the compound (I) wherein the amidino group is protected. Splitting off an amidino protecting group by a usual manner can yield the present compound (I).

The amidino protecting group may be conventionally used ones. Examples thereof include a benzyloxycarbonyl or t-butoxycarbonyl group. Examples of a method for splitting off an amidino protecting group include a reductive elimination by palladium-carbon or an elimination by trifluoroacetic acid or HBr/acetic acid.

Further, if desired, the present compound (I) can be prepared in the corresponding reduced form by the reduction of a suitable compound of formula (I) by use of a suitable reducing agent. For example, a compound of formula (I) having a nitro group is converted into a compound of formula (I) having an amino group by the reduction.

Still further, if desired, the present compound can be obtained by the removal of protective groups of amino, and hydroxyl grpoups. The protective groups, as herein referred to, include those which are commonly used, such as, for example, benzyloxycarbonyl, tert-butoxycarbonyl, benzyl and tert-butyl groups. For instance, a compound having an aminomethyl group is obtained by the removal of the protective group from a compound having a benzyloxycarbonylaminomethyl group and a compound having a hydroxyl group is obtained from a compound having a benzyloxy group.

If necessary, acid addition salts of the present compound may be prepared in a customary manner. For instance, carbonate of the present compound is dissolved or suspended in a solvent such as methanol, DMF or the like and the carbonate is allowed to dissolve by the addition of an acid such as methanesulfonic acid, hydrochloric acid or the like. To the resulting solution is added a solvent such as ethyl ether, ethyl acetate or the like to obtain a corresponding acid addition salt. Acids which can be used are pharmaceutically acceptable ones including inorganic acids such as hydrochloric acid, sulfuric acid and phosphoric acid and organic acids such as acetic acid, lactic acid, citric acid, methanesulfonic acid, succinic acid, fumaric acid and maleic acid.

The present compound and the pharmaceutically acceptable acid addition salt thereof possess powerful inhibitory activities against proteases, that is, trypsin, plasmin, kallikrein and thrombin and are effective as an anti-trypsin agent for the treatment of pancreatitis, as an anti-plasmin or anti-kallikrein agent for hemorrhagic diseases, and as an anti-thrombin agent for thrombus.

With respect to the above-mentioned proteases, their roles in a living body, the relationship to the diseases, the clinical significance of these proteases inhibitors and the significance of the tests herein performed are explained below:

I. Trypsin: Trypsin is a protease existing originally in the form of proenzyme trypsinogen in the pancreas and the proenzyme is secreted into the small intestine where it is transformed into trypsin by activation with enterokinase existing therein. Trypsin has a role as one of digestive enzymes. If the trypsinogen is activated by an chance in the pancreas to form trypsin, the pancreas tissue will be injured to manifest clinically the symptoms of pancreatitis. In fact, it is known that in an experiment using rat as test animal, when trypsin is injected conversely into the pancreas, the onset of intense pancreatitis is observed but the disease is cured by the administration of a trypsin inhibitor. From this fact, it is presumable that the present compound having a strong trypsin inhibitory activity is useful as an anti-trypsin agent which is clinically effective for the treatment of pancreatitis.

II. Plasmin: Plasmin is an enzyme existing in the blood, usually in the form of proenzyme plasminogen which is converted to plasmin by the activation with a plasminogen tissue activator such as urokinase. This enzyme acts reversely to the action of thrombin, that is, it acts to dissolve fibrin. For this reason, plasmin plays an important role in securing blood flow through capillaries. However, when this enzyme becomes abnormally activated for some reason, it causes hemorrhagic diseases. This enzyme participates also in inflammation, increasing the vascular permeability and causing edema or the like. Therefore, an inhibitor for this enzyme is useful as a drug to treat hemorrhagic diseases and inflammation.

III. Kallikrein: Kallikrein is an enzyme widely distributed in blood and other organs and glands, usually in the form of its precursor prekallikrein which is activated with Hageman factor or other proteases. This enzyme participates in the hypotensive kallikrein-kinin system which counteracts the hyper tensive renin-angitotensin system and plays an important role in the control of blood pressure. This enzyme participates also in exogenous coagulation system. Further, kallikrein originated from organs or glands plays an important role in the improvement of local circulation. However, an abnormal activation, particularly in abnormal local activation, of this enzyme causes an insufficiency of local circulation due to the exaggeration of coagulation system, causing inflammation, ulcer, or the like. Therefore, a kallikrein inhibitor is useful for the control of blood pressure and as a drug for the treatment of inflammation or ulcer.

IV. Thrombin: Thrombin is known as an enzyme having a blood coagulating activity. In normal state, thrombin is formed by the activation of prothrombin in the blood when the vascular wall is injured. Thrombin acts to decompose the fibrinogen in the blood into fibrin. The resulting fibrin deposits on the injured part of vascular wall to prevent plasma components from transudation and simultaneously to promote the restoration of tissues. However, when the coagulation system is abnormally activated for some reason, a large number of fine thrombic are formed in capillaries throughout the entire body. Therefore, the present compound is useful as a drug for the treatment of such a disease.

The present compound and its pharmaceutically acceptable acid addition salts possess a strong C1 esterase ($\overline{C1r}$, $\overline{C1s}$) inhibitory activity, an ability of inhibiting the complement mediated hemolysis, and a therapeutic activity against the Forssman shock in which the activation of the complement system caused by an immune complex is said to play an important role. This indicates that the present compound is useful as an anti-complement agent effective for the treatment of allergic diseases such as nephritis associated with the complement.

The role of complement in the living body, the interrelation between a disease and the complement, the clinical significance of inhibitor, and the significance of tests (inhibition of $\overline{C1r}$, $\overline{C1s}$, complement mediated hemolysis, and Forssman shock) performed by the present inventors are described below.

ANTI-COMPLEMENT ACTIVITY

(1) $\overline{C1r}$, $\overline{C1s}$

The complement is one of the serum components and comprises 9 components of C1 to C9. C1 is separated into 3 subcomponents of C1q, C1e,ovs/r/ and $\overline{C1s}$. $\overline{C1s0}$ and $\overline{C1r}$ mean activated C1s and activated C1r, respectively. The complement was thought at first to perform a part of the infection protective process of living body, since it shows bacteriolysis, but recently an intimate relation to the immunity has been evident. It was shown that the complement is activated by the immune complex progressively from C1 to C9 and exhibits cytolysis or hemolysis at the final stage (activation of C9). It was also disclosed that the fragments (e.g. C3a, C5a) liberated in the course of activation of the complement system exaggerate the vascular permeability and promote the chemotaxis of polymorphonuclear leucocytes or immune adherence. Since that time, the interrelationship between the abnormal activation of complement and various diseases, particularly immune diseases, has been extensively investigated and, as the result, the intimate association of autoimmune diseases with the complement is beginning to be disclosed. Examples of autoimmune diseases caused by the abnormal activation of complement include antoimmune hemolytic anemia, autoimmune thrombocytopenia, leukopenia, glomerulonephritis, systemic lupus erythematosus, serum sickness and periarteritis nodosa. It is expectable to cure such diseases by inhibiting the activation of complement or inhibiting the activated complement in an early stage. The present inventors examined the C1 esterase inhibitory effect of the present compound by using C1 esterase as target enzyme and, in addition, the influence of the present compound on the complement system to estimate the usefulness of the present compound as a drug for the treatment of autoimmune diseases.

(2) Complement mediated hemolysis

The complement mediated hemolysis is widely used as a means to determine the titration of complement. The principle of this method is based on the fact that hemolysis is caused by the activation of complement, when the latter is added to a complex (immune complex) of erythrocytes and the antibody thereof. The degree of hemolysis varies in proportion to the amount of complement added. Therefore, when a known amount of complement admixed with a C1 esterase inhibitor is used, the hemolysis must be suppressed in proportion to the inhibitory activity. The present compound having C1 esterase inhibitory activity showed strong inhibition of complement mediated hemolysis as shown hereinafter.

(3) Forssman shock

Quite different from other animals, guinea pig has on the surface of its organs a specific antigen called Forssman antigen which specifically reacts with the antibody of sheep erythrocyte. Forssman shock is based on the above principle and is a shock caused by the administration of antibody of sheep erythrocyte to a guinea pig. The Forssman shock was investigated in detail by many researches and it was definitely shown that this shock is a model case where the complement plays the principal part and that the shock is associated with a classical pathway in which the complement system is activated progressively starting from C1. Since the participation of complement in autoimmune diseases has been established, the Forssman shock can be said to be a useful means for testing a drug for autoimmune diseases. A drug effective for the treatment of Forssman shock is useful as a drug of autoimmune diseases.

[ANTI-TRYPSIN, ANTI-PLASMIN, ANTI-KALLIKREIN AND ANTI-THROMBIN ACTIVITIES]

The anti-trypsin, anti-plasmin, anti-kallikrein and anti-thrombin activities were determined according to the method of Muramatsu et al. [M. Muramatsu, T. Onishi, S. Makino, Y. Hayashi and S. Fujii, J. of Biochem., 58, 214 (1965)]. The results were as shown in Table 1. The data summarized in Table 1 are expressed in terms of molar concentration ($ID_{50}$) of the test compound which inhibits 50% of the activity of each enzyme to hydrolyze TAME (tosylalginine methyl ester). The compound No. corresponds to the compound number shown in Examples. The figure in parentheses shows the percentage inhibition at a concentration of the compound of $1 \times 10^{-5}$M. NE shows that the percentage inhibition is less than 10%.

TABLE 1

| Compound No. | Trypsin | Plasmin | Kallikrein | Thrombin |
|---|---|---|---|---|
| 1 | $1 \times 10^{-8}$ | $4 \times 10^{-7}$ | $3 \times 10^{-7}$ | $2 \times 10^{-7}$ |
| 2 | $2 \times 10^{-7}$ | $4 \times 10^{-7}$ | $3 \times 10^{-7}$ | $5 \times 10^{-7}$ |
| 3 | $4 \times 10^{-7}$ | $1 \times 10^{-6}$ | (NE) | $4 \times 10^{-7}$ |
| 4 | $2 \times 10^{-6}$ | $1 \times 10^{-6}$ | (43) | $7 \times 10^{-7}$ |
| 5 | $1 \times 10^{-7}$ | $4 \times 10^{-7}$ | $5 \times 10^{-7}$ | $3 \times 10^{-7}$ |
| 7 | $5 \times 10^{-7}$ | $3 \times 10^{-6}$ | $2 \times 10^{-6}$ | $4 \times 10^{-7}$ |
| 8 | $4 \times 10^{-7}$ | $2 \times 10^{-6}$ | $4 \times 10^{-6}$ | $6 \times 10^{-7}$ |
| 9 | $5 \times 10^{-7}$ | $9 \times 10^{-7}$ | $2 \times 10^{-6}$ | $3 \times 10^{-7}$ |
| 11 | $2 \times 10^{-7}$ | $5 \times 10^{-7}$ | $2 \times 10^{-7}$ | $3 \times 10^{-7}$ |
| 14 | $1 \times 10^{-6}$ | $3 \times 10^{-7}$ | $5 \times 10^{-6}$ | $7 \times 10^{-6}$ |
| 16 | $2 \times 10^{-6}$ | $3 \times 10^{-6}$ | (NE) | $7 \times 10^{-6}$ |
| 17 | $3 \times 10^{-6}$ | $3 \times 10^{-6}$ | (NE) | $2 \times 10^{-6}$ |
| 22 | $2 \times 10^{-7}$ | $3 \times 10^{-7}$ | $2 \times 10^{-6}$ | $2 \times 10^{-7}$ |
| 23 | $<10^{-8}$ | $3 \times 10^{-7}$ | $2 \times 10^{-6}$ | $3 \times 10^{-6}$ |
| 28 | $6 \times 10^{-6}$ | (NE) | (NE) | (NE) |
| 33 | $2 \times 10^{-7}$ | $2 \times 10^{-6}$ | $1 \times 10^{-5}$ | (40) |
| 35 | $1 \times 10^{-9}$ | $1 \times 10^{-7}$ | $1 \times 10^{-5}$ | $9 \times 10^{-8}$ |
| 38 | $9 \times 10^{-6}$ | $8 \times 10^{-7}$ | (17) | (11) |
| 42 | $2 \times 10^{-6}$ | $2 \times 10^{-6}$ | $5 \times 10^{-6}$ | (13) |
| 43 | $1 \times 10^{-7}$ | (31) | (41) | (46) |
| 45 | $5 \times 10^{-6}$ | $7 \times 10^{-6}$ | (NE) | $4 \times 10^{-6}$ |
| 50 | $6 \times 10^{-6}$ | $4 \times 10^{-6}$ | (NE) | (14) |
| 55 | $6 \times 10^{-8}$ | $3 \times 10^{-6}$ | $2 \times 10^{-6}$ | (41) |
| 61 | $3 \times 10^{-6}$ | (31) | (17) | $3 \times 10^{-6}$ |
| 65 | $8 \times 10^{-7}$ | (NE) | (NE) | (13) |

[ANTI-COMPLEMENT ACTIVITY]

(1) Anti-C1 ($C\overline{1r}$, $C\overline{1s}$) activity and inhibition of complement mediated hemolysis The anti-C1 esterase ($C\overline{1r}$, $C\overline{1s}$) activity was determined according to the method of Okamura et al. [K. Okamura, M. Muramatsu and B. Fujii, Biochem. Biophys. Acta, 295, 252-257 (1973)]. The inhibition of complement mediated hemolysis was determined according to the method of Baker et al. [B. R. Baker and E. H. Erickson, J. Med. Chem., 12, 408-414 (1969)]. The results obtained were as shown in Table 2. The figures in Table 2 have the following meanings:

$C\overline{1r}$: Molar concentration of the test compound which inhibits 50% of the ability of $C\overline{1r}$ to hydrolyse AAME (acetylarginin methyl ester) ($ID_{50}$).

$C\overline{1s}$: Molar concentration of the test compound which inhibits 50% of the ability of $C\overline{1s}$ to hydrolyse ATEE (acetyltyrosin ethyl ester) ($ID_{50}$).

The figure in parentheses shows the percent inhibition at a concentration of the compound of $1 \times 10^{-5}$M.

NE shows that the percentage inhibition is less than 10%.

Inhibition of complement mediated hemolysis (%): The inhibitory activity is shown in terms of percent inhibition of the compound at varied concentrations:

Compound No.

The compound number shown in Examples.

TABLE 2

| Compound No. | Anti-C1 activity | | Inhibition of complement mediated hemolysis (%) | | | |
|---|---|---|---|---|---|---|
| | $C\overline{1r}$ | $C\overline{1s}$ | $1 \times 10^{-4}$ | $1 \times 10^{-5}$ | $1 \times 10^{-6}$ | $1 \times 10^{-7}$ |
| 1 | $6 \times 10^{-8}$ | $2 \times 10^{-7}$ | 100 | 100 | 98 | 99 |
| 2 | $2 \times 10^{-7}$ | $4 \times 10^{-7}$ | 100 | 100 | 97 | 89 |
| 3 | $5 \times 10^{-7}$ | $4 \times 10^{-6}$ | 100 | 100 | 100 | 100 |
| 4 | $6 \times 10^{-7}$ | $3 \times 10^{-7}$ | 100 | 65 | 30 | NE |
| 5 | $3 \times 10^{-7}$ | $4 \times 10^{-7}$ | 100 | 98 | 97 | 83 |
| 7 | $3 \times 10^{-7}$ | $4 \times 10^{-6}$ | 100 | 98 | 96 | 98 |
| 8 | $1 \times 10^{-7}$ | $4 \times 10^{-6}$ | 100 | 100 | 97 | 92 |
| 9 | $3 \times 10^{-7}$ | $4 \times 10^{-6}$ | 100 | 100 | 96 | 77 |
| 11 | $2 \times 10^{-7}$ | $9 \times 10^{-7}$ | 100 | 100 | 99 | 88 |
| 14 | $3 \times 10^{-6}$ | $4 \times 10^{-7}$ | 98 | 94 | 72 | 20 |
| 16 | $4 \times 10^{-6}$ | (NE) | 100 | 99 | 99 | 98 |
| 17 | $4 \times 10^{-6}$ | $6 \times 10^{-6}$ | 100 | 100 | 95 | 90 |
| 22 | $7 \times 10^{-8}$ | $3 \times 10^{-7}$ | 100 | 96 | 58 | 34 |
| 23 | $7 \times 10^{-7}$ | $4 \times 10^{-7}$ | 100 | 99 | 95 | 91 |
| 28 | (31) | $3 \times 10^{-7}$ | 88 | 55 | 28 | NE |
| 33 | $2 \times 10^{-6}$ | $2 \times 10^{-6}$ | | | | |
| 35 | $4 \times 10^{-7}$ | $8 \times 10^{-7}$ | | | | |
| 38 | (42) | $6 \times 10^{-7}$ | | | | |
| 43 | $3 \times 10^{-7}$ | $5 \times 10^{-7}$ | | | | |
| 45 | (18) | (20) | 100 | 98 | 75 | 46 |
| 50 | $5 \times 10^{-6}$ | (18) | | | | |
| 52 | (29) | (NE) | 100 | 97 | 99 | 97 |
| 55 | $3 \times 10^{-6}$ | $4 \times 10^{-7}$ | | | | |
| 61 | $2 \times 10^{-6}$ | (16) | | | | |
| 64 | (45) | $7 \times 10^{-6}$ | | | | |
| 65 | (30) | (28) | 100 | 100 | 89 | 80 |

(2) Forssman shock

The experiment was performed according to the method of I. G. Offerness et al. [Biochem. Pharmacol., 27 (14), 1873-1878 (1978)]. Male Hartlay guinea pig of about 300 g in body weight was used. Each guinea pig of the control group was administered intravenously with hemolysin (minimum dose to cause the shock) (commercial hemolysin, 5,000 U as assayed by the method of Ogata) and the time elapsed until death was observed. For the test group, each guinea pig was administered intravenously with hemolysin after the administration of test compound (3 mg/kg) and the time elapsed until death was observed. The results obtained were as shown in Table 3.

TABLE 3

| Control group (sec.) | Group administered with compound Compound No. 1 |
|---|---|
| 278 | Survival |
| 318 | Survival |
| 296 | Survival |

Method of administration

The present compound is most suitably administered orally, though can be administered by injection. It is used as a drug either alone or in combination with other drugs. It is administered generally in the form of medicinal composition, though can be administered as simple substance without any additive. Examples of medicinal compoisition include tablets, powders, capsules, syrups and solutions. An oral composition may contain common additives such as binders, diluents, lubricants, disintegrators and excipients. Oral solutions may be in the form of aqueous or oily suspension, solution, emulsion, syrup or elixir, or in the form of dry syrup which, before use, is readjusted with water or other suitable solvents. The solutions may contain common additives such as suspending agents, flavoring agents, diluents, or emulsifies. For injection, may be used aqueous suspensions or oily suspensions.

Dosage

The present compound may be administered to mammals (including man) orally at a dose of 10 to 200 mg per day or by intravenous injection at a dose of 1 to 20 mg per day. However, these doses are presented solely for the sake of example. A suitable dose for a patient should be determined depending upon the age and body weight of the patient and the features of illness.

Examples of pharmaceutical formulations are described below.

| Examples of pharmaceutical formulations: | |
|---|---|
| (1) Capsules: | |
| The present compound | 100.0 mg |
| Lactose | 59.0 |
| Crystalline cellulose | 33.4 |
| Calcium carboxymethylcellulose | 3.6 |
| Magnesium stearate | 4.0 |
| Total | 200.0 mg |
| (2) Fine granules: | |
| The present compound | 50.0 mg |
| Lactose | 249.0 |
| Mannitol | 75.0 |
| Corn starch | 110.0 |
| Hydroxypropylcellulose | 16.0 |
| Total | 500.0 mg |
| (3) Injections: | |
| The present compound | 5.0 mg |
| Water for injection | 2 ml |

Made up to injections in a customary manner.

Toxicity

The median lethal dose ($LD_{50}$) of the present compound is as shown in Table 4.

TABLE 4

| Compound No. | $LD_{50}$ mg/kg (mouse) | |
|---|---|---|
| | I.P. | P.O. |
| 1 | 200 | 2500 |

Examples of preparation of the present compounds are described below. The physical data of each compound are summarized in Table 5.

TABLE 5

| Compound No. | $R_1$, $R_2$, $R_3$-substituted A | Z | Salt | mp. °C. | $IR\nu_{max}^{kBr}$ cm$^{-1}$ (—COO—) |
|---|---|---|---|---|---|
| 1 | 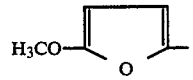 | — | MSA | 222 (d) | |
| 2 | 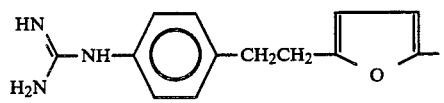 | — | 2MSA | 123–126 | |
| 3 | 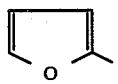 | — | MSA | 225–228 | |
| 4 | 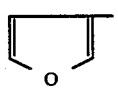 | — | MSA | 228–231 | |
| 5 | 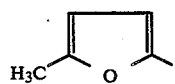 | — | MSA | 219–220 | |
| 6 | 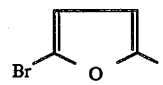 | — | MSA | 232–234 | |
| 7 | 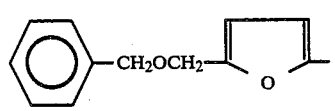 | — | MSA | 152–155 | |

TABLE 5-continued

| Compound No. | R₁, R₂, R₃-substituted A | Z | Salt | mp. °C. | IR $\nu_{max}^{KBr}$ cm⁻¹ (—COO—) |
|---|---|---|---|---|---|
| 8 | 5-(HOCH₂)-furan-2-yl | — | HBr | 213–214 | |
| 9 | 5-(CH₃COOCH₂)-furan-2-yl | — | MSA | 157–159 | |
| 10 | 5-(H₂N(HN=)C—CH₂)-furan-2-yl | — | HCl. MSA | | 1715 |
| 11 | 5-(H₃S—CH₂)-furan-2-yl | — | MSA | 192–195 | |
| 12 | 5-(O₂N—C₆H₄—CH=CH—)-furan-2-yl | — | MSA | 268–269 (d) | |
| 13 | 4-(C₆H₅CH₂OCONHCH₂)-cyclohexyl-1-(COOCH₂-furan-2-yl) | — | MSA | 209–211 | |
| 14 | furan-2-yl | —CH=CH— | MSA | 200 (d) | |
| 15 | furan-2-yl | —CH=C(C₂H₅)— | MSA | 185–188 | |
| 16 | benzofuran-2-yl | — | MSA | 215–219 | |
| 17 | 5-CH₃O-benzofuran-2-yl | — | MSA | 250–254 | |
| 18 | 6-CH₃O-benzofuran-2-yl | — | MSA | 254–256 | |
| 19 | 7-CH₃O-benzofuran-2-yl | — | MSA | 229–230 | |
| 20 | 5-(CH₃COO)-benzofuran-2-yl | — | MSA | 232–235 | |

TABLE 5-continued

| Compound No. | R₁, R₂, R₃-substituted A | Z | Salt | mp. °C. | IR$\nu_{max}^{KBr}$ cm$^{-1}$ (—COO—) |
|---|---|---|---|---|---|
| 21 | O₂N-benzofuran | — | MSA | 183–187 | |
| 22 | thiophene | — | MSA | 232–235 | |
| 23 | H₃C-thiophene | — | MSA | 206–208 | |
| 24 | thiophene | —CH₂— | MSA | 137–140 | |
| 25 | thiophene | —CH=CH— | MSA | 203–205 | |
| 26 | thiophene | —C(=N—OCH₃)— | MSA | 208 (d) | |
| 27 | benzothiophene | — | MSA | 268–270 | |
| 28 | pyrrole (NH) | — | MSA | 208 (d) | |
| 29 | pyrrole (N-CH₃) | — | MSA | 220–225 | |
| 30 | imidazole (N-COOCH₂-phenyl) | —CH=CH— | MSA | 144–145 (d) | |
| 31 | indole | — | MSA | 274–276 | |
| 32 | indole | — | MSA | 235 (d) | |

TABLE 5-continued

| Compound No. | R₁, R₂, R₃-substituted A | Z | Salt | mp. °C. | IR $\nu_{max}^{kBr}$ cm⁻¹ (—COO—) |
|---|---|---|---|---|---|
| 33 | 5-CH₃O-indole (2-yl) | — | MSA | 225–228 | |
| 34 | indol-3-yl | —CH₂— | MSA | 181–183 | |
| 35 | 5-CH₃O-2-CH₃-1-(4-chlorobenzoyl)-indol-3-yl | —CH₂— | MSA | 183–186 | |
| 36 | 5-CH₃O-2-CH₃-indol-3-yl | —CH₂— | MSA | 70–72 | |
| 37 | indol-3-yl | —CH₂CH₂— | MSA | 180–183 | |
| 38 | indol-3-yl | —CH=CH— | MSA | 185 (d) | |
| 39 | indol-3-yl | —CH₂CH₂CH₂— | MSA | 166–169 | |
| 40 | indol-3-yl (isomer) | — | MSA | 205–207 | |
| 41 | 1-(benzyloxycarbonyl)pyrrolidin-2-yl | — | MSA | 150–152 | |
| 42 | imidazol-1-yl | —CH₂phenylene | 2TsOH | >250 | |

TABLE 5-continued

| Compound No. | R₁, R₂, R₃-substituted A | Z | Salt | mp. °C. | IR$\nu_{max}^{KBr}$ cm⁻¹ (—COO—) |
|---|---|---|---|---|---|
| 43 | benzimidazole (NH) | — | MSA | 239–241 | |
| 44 | 2-methylbenzimidazole (NH) | — | MSA | 291–295 (d) | |
| 45 | 2-pyridyl | — | HCl. MSA | 121–123 | |
| 46 | 3-pyridyl | — | MSA | 207–210 | |
| 47 | 4-pyridyl | — | MSA | 182–184 | |
| 48 | 2-chloro-5-pyridyl | — | MSA | 241–243 | |
| 49 | 2-chloro-3-pyridyl | — | MSA | 234–235 | |
| 50 | 3-pyridyl | —CH=CH— | MSA | 176–179 | |
| 51 | 2-benzyloxy-5-pyridyl | — | MSA | 78–83 | |
| 52 | 2-quinolyl | — | MSA | 178–181 | |
| 53 | 3-quinolyl | — | MSA | 210–213 | |
| 54 | 2-phenyl-4-quinolyl | — | MSA | 257–259 | |

TABLE 5-continued

| Compound No. | R₁, R₂, R₃-substituted A | Z | Salt | mp. °C. | IR$\nu_{max}^{KBr}$ cm$^{-1}$ (—COO—) |
|---|---|---|---|---|---|
| 55 | C₆H₅-CH₂OCO-N-piperidyl | — | MSA | 189–190 | |
| 56 | pyrazinyl | — | MSA | 208–212 | |
| 57 | 3-phenyl-4-methyl-5-methyl-isoxazolyl | — | MSA | 233–235 | |
| 58 | H₅C₂O-C(=CH-N)-O-C(CH₃) | — | MSA | 184–187 (d) | |
| 59 | benzothiazolyl | — | MSA | 223–225 | |
| 60 | 3-methylcoumarin-2-one | — | MSA | 257 (d) | |
| 61 | 10-methylphenothiazinyl | —CH₂— | MSA | 200–203 | |
| 62 | 2-pyrrolidinyl (NH) | — | 2HBr | 192–196 | |
| 63 | H₂NCH₂-cyclohexyl-COOCH₂-furyl | — | 2HBr | 152–155 | |
| 64 | 4-piperidyl (HN) | — | 2HBr | >240 | |
| 65 | 5-nitro-2-methylfuryl (O₂N) | — | TFA | 220 (d) | |
| 66 | (H₃C)₂S⁺—CH₂-furyl ClO₄⁻ | — | HBR | | 1730 |

MSA shows methanesulfonate.
TsOH shows toluenesulfonate.
TFA shows trifluoroacetate.

EXAMPLE 1 (COMPOUND NO. 1)

Synthesis of 6-amidino-2-naphthyl 5-methoxy-furan-2-carboxylate

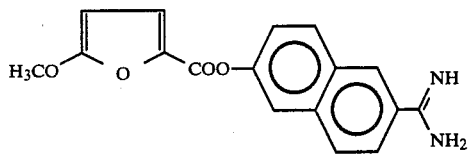

In 10 ml of dry pyridine was dissolved 1.4 g of 5-methoxy-furan-2-carboxylic acid. To the resulting solution was added 2.5 g of DCC and the reaction mixture was stirred for 30 minutes at room temperature. To the reaction mixture was added with stirring and cooling in ice 2.8 g of 6-amidino-2-naphthol methanesulfonate. The reaction mixture was stirred overnight at room temperature. The precipitate was collected by filtration, washed with dry pyridine, added to DMF and stirred. The insolubles were filtered off and ethyl ether was added to the filtrate. The precipitate was collected by filtration and washed with acetone to obtain 2.7 g of 6-amidino-2-naphthyl 5-methoxy-furan-2-carboxylate methanesulfonate.

EXAMPLE 2 (COMPOUND NO. 2)

Synthesis of 6-amidino-2-naphthyl 5-(p-guanidinophenylethyl)-furan-2-carboxylate

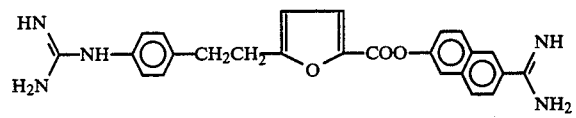

To 2.9 g of 5-(p-guanidinophenylethyl)-furan-2-carboxylic acid methanesulfonate, 2.2 g of 6-amidino-2-naphthol methanesulfonate and 1.9 g of DCC was added 15 ml of anhydrous pyridine. The reaction mixture was stirred overnight at room temperature. The insolubles were filtered off and the filtrate was added to 100 ml of ethyl ether with stirring. Decantation is conducted to remove the ethyl ether. After repeating the procedure several times, the filtrate was dissolved in a small amount of methanol and the resulting solution was added to a saturated aqueous sodium hydrogencarbonate solution while stirring. The insolubles which were precipitated were collected by filtration and washed with water and acetone. The precipitate was suspended in a small amount of methanol and methanesulfonic acid was added to the resulting suspension. The insolubles were filtered off and the filtrate was added with stirring to 100 ml of ethyl ether. The ethyl ether was removed by decantation. After repeating the procedure several times, acetone was added to the filtrate. The mixture was stirred and decanted to remove the acetone. To the resulting mixture was added a small amount of ethanol and isopropanol and stirred. A pale yellow solid which was precipitated was collected by filtration to give 2.5 g of 6-amidino-2-naphthyl 5-(p-guanidinophenylethyl)-furan-2-carboxylate dimethanesulfonate.

Compounds Nos. 3 to 61 were obtained as in Examples 1 and 2.

EXAMPLE 3 (COMPOUND NO. 62)

Synthesis of 6-amidino-2-naphthyl pyrrolidine-2-carboxylate

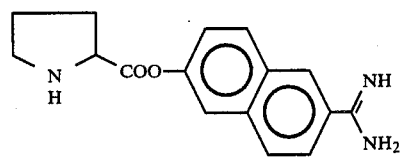

To a solution of 1.5 g of 6-amidino-2-naphthyl 1-benzyloxycarbonylpyrrolidine-2-carboxylate methanesulfonate in 10 ml of acetic acid, was added 1 ml of anisole. To the mixture, while cooling in ice and stirring, was added 3 ml of a 30% HBr/acetic acid solution. Thereafter the resulting mixture was stirred overnight at room temperature. The precipitate was collected by filtration and washed sufficiently with ethyl ether and acetone. Recrystallization from a mixture of methanol and ethyl ether gave 1.1 g of 6-amidino-2-naphthyl pyrrolidine-2-carboxylate dihydrobromide.

Compound Nos. 63 and 64 were obtained as in Example 3.

EXAMPLE 4 (COMPOUND NO. 65)

Synthesis of 6-amidino-2-naphthyl 5-nitrofuran-2-carboxylate

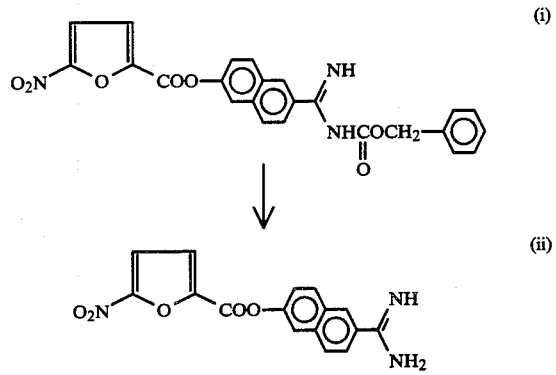

Synthesis of compound (i)

To a solution of 1.2 g of 5-nitrofuran-2-carboxylic acid in 15 ml of ethyl acetate, was added 2.5 g of phosphorous pentachloride. The resulting mixture was stirred for 45 minutes at room temperature. Distilling off the solvent gave the oily substance, 5-nitrofuran-2-carboxylic acid chloride.

To a solution of 3.2 g of 6-(benzyloxycarbonylaminoiminomethyl)-2-naphthol in 40 ml of ethyl acetate, was added 1.2 g of triethylamine. To the resulting solution, while cooling in ice and stirring, was added 5-nitrofuran-2-carboxylic acid chloride. Thereafter the mixture was stirred overnight at room temperature. The precipitate was collected by filtration and washed with water to obtain 4.4 g of 6-(benzyloxycarbonylaminoiminomethyl)-2-naphthyl 5-nitrofuran-2-carboxylate, m.p.: 109°–112° C.

Synthesis of compound (ii) from Compound (i)

To 460 mg of 6-(benzyloxycarbonylaminoiminomethyl)-2-naphthyl 5-nitrofuran-2-carboxylate, while cooling in ice and stirring, were added 2 ml of trifluoroacetic acid and three drops of anisole. The mixture was stirred overnight at 35° C. To the resulting yellow clear solution was added ethyl ether. The precipitated yellow powders were collected by filtration and washed with ethyl ether and acetone to obtain 400 mg of 6-amidino-2-naphthyl 5-nitrofuran-2-carboxylate trifluoroacetate.

Compound No. 66 was obtained as in Example 4.

What is claimed is:

1. Amidine compounds of formula (I)

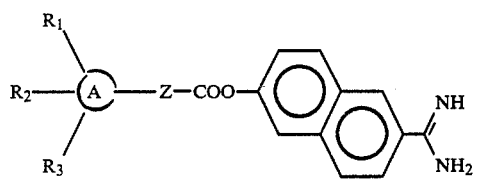

wherein $R_1$, $R_2$ and $R_3$ represent each a hydrogen atom, $R_4$, halogen, $NO_2$,

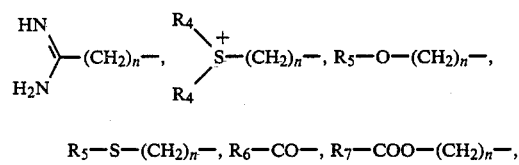

$R_5-S-(CH_2)_n-$, $R_6-CO-$, $R_7-COO-(CH_2)_n-$,

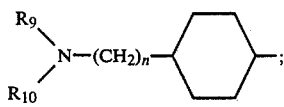

$R_4$ represents a $C_1$ to $C_4$ straight or branched chain alkyl group;

$R_5$ represents a hydrogen atom, a $C_1$ to $C_4$ straight or branched chain alkyl or benzyl group;

$R_6$ represents a $C_1$ to $C_4$ straight or branched chain alkyl group,

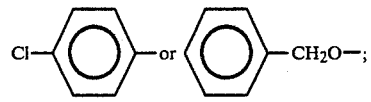

$R_7$ represents a $C_1$ to $C_4$ straight or branched chain alkyl group or

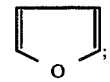

$R_8$ represents a hydrogen atom, $NO_2$ or a guanidino group;

X represents a single bond, $-(CH_2)_2-$ or $-CH=CH-$;

n is 0 to 4;

$R_9$ and $R_{10}$ each represent a hydrogen atom or $R_{12}CO-$, wherein $R_{12}$ represents a $C_1$ to $C_4$ straight or branched chain alkyl group, a benzyloxycarbonyl or t-butoxycarbonyl group;

Z represents a single bond, a $C_1$ to $C_4$ straight or branched chain alkylene, a $C_1$ to $C_4$ straight or branched chain alkenylene or a $C_1$ to $C_4$ straight or branched chain alkynylene group; and A represents and pharmaceutically acceptable acid addition salts thereof.

* * * * *